United States Patent
Gehring et al.

Patent Number: 4,734,122
Date of Patent: Mar. 29, 1988

[54] SUBSTITUTED 5-ACYLAMINO-1-PHENYLPYRAZOLES COMPOSITION CONTAINING THEM, AND HERBICIDAL METHOD OF USING THEM

[75] Inventors: Reinhold Gehring; Jörg Stetter, both of Wuppertal; Otto Schallner, Monheim; Ludwig Eue, Leverkusen; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 743,459

[22] Filed: Jun. 11, 1985

[30] Foreign Application Priority Data

Jun. 27, 1984 [DE] Fed. Rep. of Germany ....... 3423582

[51] Int. Cl.⁴ .................. A01N 43/56; C07D 231/40
[52] U.S. Cl. .......................... 71/92; 548/362; 548/377
[58] Field of Search .............. 548/362, 377; 21/92

[56] References Cited

U.S. PATENT DOCUMENTS

3,646,059  2/1972  Brantley ............................. 548/362

FOREIGN PATENT DOCUMENTS

0034945  9/1981  European Pat. Off. ............... 71/92
0053698  6/1982  European Pat. Off. ............... 71/92
0071794  2/1983  European Pat. Off. ............... 71/92
8200212  2/1982  United Kingdom ................... 71/92
2101999  1/1983  United Kingdom ................... 71/92

Primary Examiner—Richard A. Schwartz
Assistant Examiner—Kurt G. Briscoe
Attorney, Agent, or Firm—Sprung Horn Kramer & Woods

[57] ABSTRACT

5-acylamino-1-phenylpyrazole herbicides of the formula

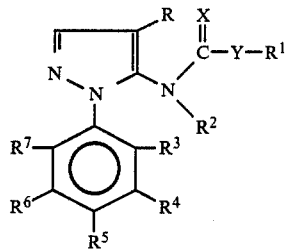

in which
R represents cyano, alkoxycarbonyl, alkenyloxycarbonyl, alkinyloxycarbonyl, aminocarbonyl, alkylaminocarbonyl, alkenylaminocarbonyl or alkinylaminocarbonyl,
$R^1$ represents alkyl, alkenyl, alkinyl, alkoxyalkyl, alkylthioalkyl, halogenoalkyl, cycloalkyl or optionally substituted aryl, and, in the case in which Y represents the

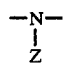

group, also represents hydrogen,
X represents oxygen or sulphur,
Y represents oxygen, sulphur or the

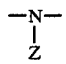

group,
wherein
Z represents hydrogen, alkyl, alkoxy, alkenyl, alkinyl or optionally substituted aryl,
$R^2$ represents hydrogen or the radical

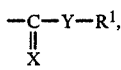

and
$R^3$, $R^4$, $R^5$, $R^6$ and $R^7$, which are identical or different, represent hydrogen, halogen, cyano, nitro, alkyl, alkoxy, alkylsulphonyl, alkoxycarbonyl or a radical $-(X')_n-R^8$,
wherein
X' represents oxygen, sulphur, sulphinyl or sulphonyl,
n represents 0 or 1 and
$R^8$ represents halogenoalkyl, with the proviso that at least one of the radicals $R^3$, $R^4$, $R^5$, $R^6$ or $R^7$ represents a radical $-(X')_n-R^8$, but R does not represent cyano when $R^5$ represents trifluoromethyl.

9 Claims, No Drawings

SUBSTITUTED 5-ACYLAMINO-1-PHENYLPYRAZOLES COMPOSITION CONTAINING THEM, AND HERBICIDAL METHOD OF USING THEM

The invention relates to new substituted 5-acylamino-1-phenylpyrazoles, several processes for their preparation, and their use as herbicides.

It is already known that certain substituted 5-acylamino-1-phenylpyrazoles, such as, for example, 4-cyano-5-propionamido-1-(2,4,6-trichlorophenyl)-pyrazole, possess herbicidal properties (see, for example, DE-OS (German Published Specification) No. 3,226,513).

However, the herbicidal action of these known compounds against weeds, as well as their toleration by important crop plants, is not always completely satisfactory in all fields of use.

New substituted 5-acylamino-1-phenylpyrazoles of the general formula (I)

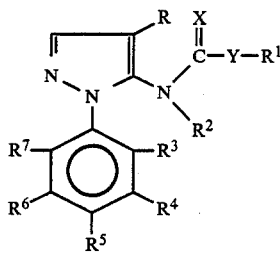

in which

R represents cyano, alkoxycarbonyl, alkenyloxycarbonyl, alkinyloxycarbonyl, aminocarbonyl, alkylaminocarbonyl, alkenylaminocarbonyl or alkinylaminocarbonyl, $R^1$ represents alkyl, alkenyl, alkinyl, alkoxyalkyl, alkylthioalkyl, halogenalkyl, cycloalkyl or optionally substituted aryl, and, in the case in which Y represents the

group, also represents hydrogen,

X represents oxygen or sulphur,

Y represents oxygen, sulphur or the

group, wherein

Z represents hydrogen, alkyl, alkoxy, alkenyl, alkinyl or optionally substituted aryl, $R^2$ represents hydrogen or the radical

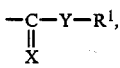

and $R^3$, $R^4$, $R^5$, $R^6$ and $R^7$, which are identical or different, represent hydrogen, halogen, cyano, nitro, alkyl, alkoxy, alkylsulphonyl, alkoxycarbonyl or a radical $—(X')_n—R^8$, wherein X' represents oxygen, sulphur, sulphinyl or sulphonyl, n represents 0 or 1 and $R^8$ represents halogenoalkyl, with the proviso that at least one of the radicals $R^3$, $R^4$, $R^5$, $R^6$ or $R^7$ represents a radical $—(X')_n—R^8$, but R does not represent cyano when $R^5$ represents trifluoromethyl, have been found.

Furthermore, it has been found that the new substituted 5-acylamino-1-phenylpyrazoles of the general formula (I) are obtained when (a) 5-amino-pyrazoles of the formula (II)

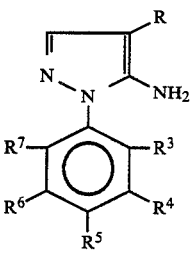

in which

R, $R^3$, $R^4$, $R^5$, $R^6$ and $R^7$ have the meaning given above, ($\alpha$) are reacted with acylating agents of the formula (III)

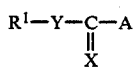

in which $R^1$, X and Y have the meaning given above and

A represents an activating leaving group, if appropriate in the presence of a diluent and, if appropriate, in the presence of an acid-binding agent, or ($\beta$) are reacted with iso(thio)cyanates of the formula (IV)

$$R^1—N=C=X \qquad (IV)$$

in which $R^1$ and X have the meaning given above, if appropriate also in the presence of a diluent and, if appropriate, in the presence of a basic catalyst, or when (b) the biscarbamates obtainable by process (a-$\alpha$), of the formula (Ia)

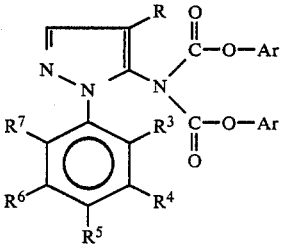

in which

Ar represents optionally substituted aryl and

R, $R^3$, $R^4$, $R^5$, $R^6$ and $R^7$ have the meaning given above, are reacted with alcohols, amines or thiols of the formula (V)

$$R^1—Y—H \qquad (V)$$

in which $R^1$ and Y have the meaning given above, if appropriate in the presence of a diluent and, if appropriate, in the presence of a basic catalyst.

Finally, it has been found that the new substituted 5-acylamino-1-phenylpyrazoles of the formula (I) possess herbicidal properties, in particular selective herbicidal properties.

Surprisingly, the new substituted 5-acylamino-1-phenyl-pyrazoles of the formula (I) possess a better herbicidal activity against weeds, coupled with better toleration by important useful plants, than, for example, 4-cyano-5-propionamido-1-(2,4,6-trichlorophenyl)-pyrazole, which is known from the prior art and is a similar compound chemically and in terms of its action.

Formula (I) gives a general definition of the new substituted 5-acyl-amino-1-phenylpyrazoles. Preferred compounds of the formula (I) are those in which R represents cyano or aminocarbonyl, or alkoxycarbonyl, alkenyloxycarbonyl, alkinyloxycarbonyl, alkylaminocarbonyl, alkenylaminocarbonyl or alkinylaminocarbonyl, each of which is straight-chain or branched and each of which has up to 4 carbon atoms in the individual alkyl parts, $R^1$ represents alkyl, alkenyl, alkinyl, alkoxyalkyl or alkylthioalkyl, each of which is straight-chain or branched and each of which has up to 6 carbon atoms in the individual alkyl or alkenyl or alkinyl parts, and furthermore represents straight-chain or branched halogenoalkyl having 1 to 6 carbon atoms and 1 to 9 identical or different halogen atoms, and furthermore represents cycloalkyl having 3 to 7 carbon atoms, or aryl which has 6 to 10 carbon atoms and is optionally monosubstituted or polysubstituted by identical or different substituents, suitable substituents being: halogen, cyano, nitro, or alkyl, alkoxy, alkylthio or alkoxycarbonyl, each of which is straight-chain or branched and each of which has up to 4 carbon atoms in the individual alkyl parts, or in the case in which Y represents the $$-\underset{\underset{Z}{|}}{N}-$$

group, also represents hydrogen,

X represents oxygen or sulphur,

Y represents oxygen, sulphur or the $$-\underset{\underset{Z}{|}}{N}-$$

group, wherein

Z represents hydrogen or alkyl, alkoxy, alkenyl or alkinyl, each of which is straight-chain or branched and each of which has up to 4 carbon atoms, or represents aryl which has 6 to 10 carbon atoms and is optionally monosubstituted or polysubstituted by identical or different substituents, suitable aryl substituents being those mentioned in the case of $R^1$, $R^2$ represents hydrogen or the radical $$-\underset{\underset{}{\overset{\overset{X}{\|}}{C}}}-Y-R^1$$

and $R^3$, $R^4$, $R^5$, $R^6$ and $R^7$ independently of one another represent hydrogen, fluorine, chlorine, bromine, iodine or nitro, or alkyl, alkoxy, alkylsulphonyl or alkoxycarbonyl, each of which is straight-chain or branched and has up to 4 carbon atoms in the particular alkyl parts, or represents a radical —(X')$_n$—$R^8$, wherein X' represents oxygen, sulphur, sulphinyl or sulphonyl, n represents 0 or 1 and $R^8$ represents straight-chain or branched halogenoalkyl having up to 4 carbon atoms and up to 9 identical or different halogen atoms, with the proviso that at least one of the radicals $R^3$, $R^4$, $R^5$, $R^6$ or $R^7$ represents a radical —(X')$_n$—$R^8$, but R does not represent cyano when $R^5$ represents trifluoromethyl.

Particularly preferred compounds of the formula (I) are those in which

R represents cyano, methoxycarbonyl, ethoxycarbonyl, allyloxycarbonyl, propargyloxycarbonyl, aminocarbonyl, methylaminocarbonyl, dimethylaminocarbonyl, ethylaminocarbonyl, diethylaminocarbonyl, diallylaminocarbonyl or dipropargylaminocarbonyl, $R^1$ represents methyl, ethyl, n- and i-propyl, n-, i-, s- and t-butyl, cyclopropyl, 2,2-dichlorocyclopropyl, 2,2-dichloro-1-methylcyclopropyl, methylthiomethyl, cyclopentyl, cyclohexyl, ethoxymethyl, methoxymethyl, ethoxyethyl, chloromethyl, dichloromethyl, trichloromethyl, trifluoromethyl, dichlorofluoromethyl, difluorochloromethyl or pentafluoroethyl, or represents phenyl which is optionally monosubstituted to trisubstituted by identical or different substituents from amongst fluorine, chlorine, bromine, nitro, methyl and methoxy, or, in the case in which Y represents the $$-\underset{\underset{Z}{|}}{N}-$$

group, also represents hydrogen,

X represents oxygen or sulphur,

Y represents oxygen, sulphur or the $$-\underset{\underset{Z}{|}}{N}-$$

group, wherein

Z represents hydrogen, methyl, ethyl, n- or i-propyl, n- i-, s- or t-butyl, methoxy, ethoxy, allyl or propargyl, or represents phenyl which is optionally monosubstituted to trisubstituted by identical or different substituents, suitable phenyl substituents being those mentioned in the case of $R^1$, $R^2$ represents hydrogen or the radical

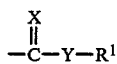

and $R^3$, $R^4$, $R^5$, $R^6$ and $R^7$ independently of one another represent hydrogen, fluorine, chlorine, bromine, cyano, nitro, methyl, ethyl, n- and i-propyl, methoxy, ethoxy, methylsulphonyl, methoxycarbonyl, ethoxycarbonyl or a radical $-(X')_n-R^8$
wherein
 $X'$ represents oxygen, sulphur, sulphinyl or sulphonyl,
 n represents 0 or 1 and
 $R^8$ represents trifluoromethyl, trichloromethyl, dichlorofluoromethyl, difluorochloromethyl, dichloromethyl, chloromethyl, difluoromethyl, pentafluoroethyl, tetrafluoroethyl, trifluorochloroethyl, trifluoroethyl, difluorodichloroethyl, trifluorodichloroethyl or pentachloroethyl, with the proviso that at least one of the radicals $R^3$, $R^4$, $R^5$, $R^6$ or $R^7$ represents a radical $-(X')_n-R^8$, but R does not represent cyano when $R^5$ represents trifluoromethyl.

In addition to the compounds mentioned in the preparation examples, the following compounds of the general formula (I) may be mentioned individually:

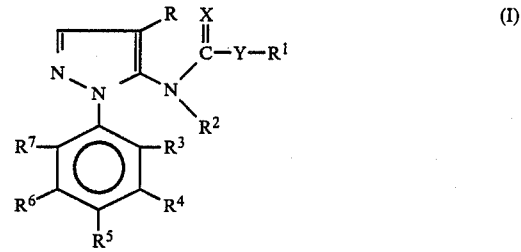

TABLE 1

| R | $R^1$ | $R^2$ | $R^3$ | $R^4$ | $R^5$ | $R^6$ | $R^7$ | X | Y |
|---|---|---|---|---|---|---|---|---|---|
| CN | CH₃ | H | F | H | OCF₃ | H | H | O | O |
| CN | CH₃ | H | F | H | OCF₃ | H | F | O | O |
| CN | CH₃ | H | F | F | OCF₃ | F | F | O | O |
| CN | CH₃ | H | Cl | H | OCF₃ | H | H | O | O |
| CN | CH₃ | H | Cl | H | OCF₃ | H | Cl | O | O |
| CN | CH₃ | H | Cl | Cl | OCF₃ | H | H | S | O |
| CN | CH₃ | H | Cl | H | OCF₃ | H | F | O | N—CH₃ |
| CN | CH₃ | H | Br | H | OCF₃ | H | H | O | S |
| CN | CH₃ | H | Br | H | OCF₃ | H | Br | O | O |
| CN | C₂H₅ | F | H | H | OCF₃ | H | H | O | N—CH₃ |
| CN | C₂H₅ | H | F | H | OCF₃ | H | F | O | O |
| CN | C₂H₅ | H | F | F | OCF₃ | F | F | O | N—CH₃ |
| CN | C₂H₅ | CH₃ | Cl | H | OCF₃ | H | H | O | O |
| CN | C₂H₅ | H | Cl | Cl | OCF₃ | H | H | O | N—CH₃ |
| CN | C₂H₅ | H | Cl | H | OCF₃ | H | F | O | O |
| CN | C₂H₅ | H | Br | H | OCF₃ | H | H | O | S |
| CN | C₂H₅ | H | Br | H | OCF₃ | H | Br | O | S |
| CN | C₂H₅ | CH₃ | Cl | H | OCF₃ | H | Cl | O | O |
| CN | ▷◁H | H | F | H | OCF₃ | H | H | O | O |
| CN | ▷◁H | CH₃ | F | H | OCF₃ | H | F | O | O |
| CN | ▷◁H | H | F | F | OCF₃ | F | F | O | N—OCH₃ |
| CN | ▷◁H | H | Cl | H | OCF₃ | H | H | O | S |
| CN | ▷◁H | H | Cl | H | OCF₃ | H | Cl | O | O |
| CN | ▷◁H | H | Cl | Cl | OCF₃ | H | H | O | O |
| CN | ▷◁H | H | Cl | H | OCF₃ | H | F | O | S |
| CN | ▷◁H | H | Br | H | OCF₃ | H | H | O | N—CH₃ |
| CN | ▷◁H | H | Br | H | OCF₃ | H | Br | O | N—CH₃ |

TABLE 1-continued

| R | R¹ | R² | R³ | R⁴ | R⁵ | R⁶ | R⁷ | X | Y |
|---|---|---|---|---|---|---|---|---|---|
| CN | CH₃ | H | Cl | H | SCH₂CF₃ | H | H | O | S |
| CN | CH₃ | H | Cl | H | SCH₂CF₃ | H | Cl | O | S |
| CN | CH₃ | H | Br | H | SCH₂CF₃ | H | H | O | O |
| CN | CH₃ | H | Br | H | SCH₂CF₃ | H | Br | O | O |
| CN | CH₃ | H | Cl | Cl | SCH₂CF₃ | H | H | O | O |
| CN | C₂H₅ | H | Cl | H | SCH₂CF₃ | H | H | O | O |
| CN | C₂H₅ | H | Cl | H | SCH₂CF₃ | H | Cl | O | O |
| CN | C₂H₅ | H | Br | H | SCH₂CF₃ | H | H | O | N—CH₃ |
| CN | C₂H₅ | H | Br | H | SCH₂CF₃ | H | Br | O | O |
| CN | C₂H₅ | H | Cl | Cl | SCH₂CF₃ | H | H | O | O |
| CN | cyclopropyl | H | Cl | H | SCH₂CF₃ | H | H | O | O |
| CN | cyclopropyl | H | Cl | H | SCH₂CF₃ | H | Cl | O | N—CH₃ |
| CN | cyclopropyl | H | Br | H | SCH₂CF₃ | H | H | O | N—CH₃ |
| CN | cyclopropyl | H | Br | H | SCH₂CF₃ | H | Br | O | S |
| CN | cyclopropyl | H | Cl | Cl | SCH₂CF₃ | H | H | O | S |
| cn | CH₃OCH₂ | H | Cl | H | SCH₂CF₃ | H | H | O | S |
| CN | CH₃OCH₂ | H | Cl | H | SCH₂CF₃ | H | Cl | O | N—CH₃ |
| CN | CH₃OCH₂ | H | Br | H | SCH₂CF₃ | H | H | O | N—CH₃ |
| CN | CH₃OCH₂ | H | Br | H | SCH₂CF₃ | H | Br | O | O |
| CN | CH₃OCH₂ | H | Cl | Cl | SCH₂CF₃ | H | H | O | O |
| CN | CH₃ | H | Cl | H | OCH₂CF₃ | H | H | O | O |
| CN | CH₃ | H | Cl | H | OCH₂CF₃ | H | Cl | O | N—CH₃ |
| CN | CH₃ | H | Br | H | OCH₂CF₃ | H | H | O | O |
| CN | CH₃ | H | Br | H | OCH₂CF₃ | H | Br | O | O |
| CN | C₂H₅ | H | Cl | H | OCH₂CF₃ | H | H | O | N—CH₃ |
| CN | C₂H₅ | H | Cl | H | OCH₂CF₃ | H | Cl | O | S |
| CN | C₂H₅ | H | Br | H | OCH₂CF₃ | H | H | O | S |
| CN | C₂H₅ | H | Br | H | OCH₂OCF₃ | H | Br | O | N—CH₃ |
| CN | cyclopropyl | H | Cl | H | OCH₂CF₃ | H | H | O | O |
| CN | cyclopropyl | H | Cl | H | OCH₂CF₃ | H | Cl | O | S |
| CN | cyclopropyl | H | Br | H | OCH₂CF₃ | H | H | O | S |
| CN | cyclopropyl | H | Br | H | OCH₂CF₃ | H | Br | O | N—CH₃ |
| CN | CH₃OCH₂— | H | Cl | H | OCH₂CF₃ | H | H | O | O |
| CN | CH₃OCH₂— | H | Cl | H | OCH₂CF₃ | H | Cl | O | O |
| CN | CH₃OCH₂— | H | Br | H | OCH₂CF₃ | H | H | O | O |
| CN | CH₃OCH₂— | H | Br | H | OCH₂CF₃ | H | Br | O | O |
| CN | CH₃ | H | SCF₃ | H | Cl | H | H | O | S |
| CN | C₂H₅ | H | SCF₃ | H | Cl | H | H | O | S |
| CN | CH₃ | H | SCF₃ | H | Cl | H | Cl | O | N—CH₃ |
| CN | C₂H₅ | H | SCF₃ | H | Cl | H | Cl | O | S |
| CN | CH₃ | H | Cl | H | SO₂CH₂CF₃ | H | Cl | O | O |
| CN | CH₃ | H | Cl | H | SO₂CH₂CF₃ | H | Cl | O | N—CH₃ |
| CN | C₂H₅ | H | Cl | H | SO₂CH₂CF₃ | H | Cl | O | O |
| CN | C₂H₅ | H | Cl | H | SO₂CH₂CF₃ | H | Cl | O | N—CH₃ |
| CN | CH₃ | H | F | H | SCF₃ | H | H | O | O |
| CN | CH₃ | H | F | H | SCF₃ | H | F | O | O |
| CN | CH₃ | H | F | F | SCF₃ | F | F | O | O |
| CN | CH₃ | H | Cl | H | SCF₃ | H | H | O | N—CH₃ |
| CN | CH₃ | H | Cl | H | SCF₃ | H | CL | O | N—CH₃ |
| CN | CH₃ | H | Cl | Cl | SCF₃ | H | H | O | S |

TABLE 1-continued

| R | R¹ | R² | R³ | R⁴ | R⁵ | R⁶ | R⁷ | X | Y |
|---|---|---|---|---|---|---|---|---|---|
| CN | CH₃ | H | Cl | H | SCF₃ | H | F | O | S |
| CN | CH₃ | H | Br | H | SCF₃ | H | H | O | O |
| CN | CH₃ | H | Br | H | SCF₃ | H | Br | O | O |
| CN | C₂H₅ | H | F | H | SCF₃ | H | H | O | O |
| CN | C₂H₅ | H | F | H | SCF₃ | H | F | O | N—CH₃ |
| CN | C₂H₅ | H | F | H | SCF₃ | F | F | O | N—CH₃ |
| CN | C₂H₅ | H | Cl | H | SCF₃ | H | H | O | O |
| CN | C₂H₅ | H | Cl | H | SCF₃ | H | Cl | O | O |
| CN | C₂H₅ | H | Cl | H | SCF₃ | H | F | O | O |
| CN | C₂H₅ | H | Br | H | SCF₃ | H | H | O | S |
| CN | c-C₃H₅ | H | F | H | SCF₃ | H | H | O | S |
| CN | c-C₃H₅ | H | F | H | SCF₃ | H | F | O | S |
| CN | c-C₃H₅ | H | F | F | SCF₃ | F | F | O | N—CH₃ |
| CN | c-C₃H₅ | H | Cl | H | SCF₃ | H | H | O | N—CH₃ |
| CN | c-C₃H₅ | H | Cl | H | SCF₃ | H | Cl | O | O |
| CN | c-C₃H₅ | H | Cl | Cl | SCF₃ | H | H | O | O |
| CN | c-C₃H₅ | H | Cl | H | SCF₃ | H | F | O | O |
| CN | c-C₃H₅ | H | Br | H | SCF₃ | H | H | O | S |
| CN | c-C₃H₅ | H | Br | H | SCF₃ | H | Br | O | S |
| CN | H | H | CF₃ | H | SO₂CH₃ | H | H | O | O |
| CN | H | H | CF₃ | H | SO₂CH₃ | H | H | O | S |
| CN | H | H | CF₃ | H | SCF₃ | H | H | O | N—CH₃ |
| CN | H | H | OCF₃ | H | OCF₃ | H | H | O | S |
| CN | CH₃ | H | CF₃ | H | SO₂CH₃ | H | H | O | O |
| CN | CH₃ | H | CF₃ | H | SO₂CH₃ | H | H | O | O |
| CN | CH₃ | H | CF₃ | H | SCF₃ | H | H | O | O |
| CN | CH₃ | H | OCF₃ | H | OCF₃ | H | H | O | S |
| CN | C₂H₅ | H | CF₃ | H | SO₂CH₃ | H | H | O | N—CH₃ |
| CN | C₂H₅ | H | CF₃ | H | SO₂CH₃ | H | H | O | S |
| CN | C₂H₅ | H | CF₃ | H | SCF₃ | H | H | O | O |
| CN | C₂H₅ | H | OCF₃ | H | OCF₃ | H | H | O | N—CH₃ |
| CN | c-C₃H₅ | H | CF₃ | H | SO₂CH₃ | H | H | O | O |
| CN | c-C₃H₅ | CH₃ | CF₃ | H | SO₂CH₃ | H | H | O | O |
| CN | c-C₃H₅ | C₂H₅ | CF₃ | H | SCF₃ | H | H | O | O |
| CN | c-C₃H₅ | C₃H₇ | OCF₃ | H | OCF₃ | H | H | O | O |
| CN | H | H | Cl | H | SO₂CH₂CF₃ | H | H | O | N—CH₃ |
| CN | H | H | Cl | H | SO₂CH₂CF₃ | H | H | O | N—C₂H₅ |
| CN | CH₃ | CH₃ | Cl | H | SCHF₂ | H | H | O | O |
| CN | CH₃ | C₂H₅ | Cl | H | SCH₂F | H | Cl | O | O |
| CN | CH₃ | C₃H₇ | Br | H | SCHF₂ | H | H | O | O |

TABLE 1-continued

| R | R¹ | R² | R³ | R⁴ | R⁵ | R⁶ | R⁷ | X | Y |
|---|---|---|---|---|---|---|---|---|---|
| CN | CH₃ | H | Br | H | SCHF₂ | H | Br | O | N—CH₃ |
| CN | C₂H₅ | CH₃ | Cl | H | SCH₂F | H | H | O | S |
| CN | C₂H₅ | C₂H₅ | Cl | H | SCHF₂ | H | Cl | O | S |
| CN | C₂H₅ | C₂H₅ | Br | H | SCHF₂ | H | H | O | N—CH₃ |
| CN | C₂H₅ | C₃H₇ | Br | H | SCHF₂ | H | Br | O | S |
| CN |  | C₃H₇ | Cl | H | SCHF₂ | H | H | O | N—CH₃ |
| CN |  | H | Cl | H | SCHF₂ | H | Cl | O | S |
| CN |  | CH₃ | Br | H | SCHF₂ | H | H | O | S |
| CN |  | C₃H₇ | Br | H | SCHF₂ | H | Br | O | N—CH₃ |
| CN | CH₃ | H | Cl | H | SCF₂CHF₂ | H | H | O | O |
| CN | CH₃ | H | Cl | H | SCF₂CHF₂ | H | Cl | O | S |
| CN | CH₃ | H | Br | H | SCF₂CHF₂ | H | H | O | N—CH₃ |
| CN | CH₃ | CH₃ | Br | H | SCF₂CHF₂ | H | Br | O | O |
| CN | C₂H₅ | CH₃ | Cl | H | SCF₂CHF₂ | H | H | O | S |
| CN | C₂H₅ | CH₃ | Cl | H | SCF₂CHF₂ | H | Cl | O | N—CH₃ |
| CN | C₂H₅ | C₂H₅ | Br | H | SCF₂CHF₂ | H | H | O | O |
| CN | C₂H₅ | C₂H₅ | Br | H | SCF₂CHF₂ | H | Br | O | S |
| CN |  | C₂H₅ | Cl | H | SCF₂CHF₂ | H | H | O | N—CH₃ |
| CN |  | C₃H₇ | Cl | H | SCF₂CHF₂ | H | Cl | O | O |
| CN |  | C₃H₇ | Br | H | SCF₂CHF₂ | H | H | O | S |
| CN |  | C₃H₇ | Br | H | SCF₂CHF₂ | H | Br | O | N—CH₃ |
| CN | CH₃ | H | Cl | H | SCF₂CHFCl | H | H | O | O |
| CN | CH₃ | H | Cl | H | SCF₂CHFCl | H | Cl | O | O |
| CN | CH₃ | H | Br | H | SCF₂CHFCl | H | H | O | S |
| CN | CH₃ | H | Br | H | SCF₂CHFCl | H | Br | O | O |
| CN | C₂H₅ | H | Cl | H | SCF₂CHFCl | H | H | O | S |
| CN | C₂H₅ | H | Cl | H | SCF₂CHFCl | H | Cl | O | S |
| CN | C₂H₅ | H | Br | H | SCF₂CHFCl | H | H | O | S |
| CN | C₂H₅ | H | Br | H | SCF₂CHFCl | H | Br | O | N—CH₃ |
| CN |  | H | Cl | H | SCF₂CHFCl | H | H | O | O |
| CN |  | H | Cl | H | SCF₂CHFCl | H | Cl | O | N—CH₃ |
| CN |  | H | Br | H | SCF₂CHFCl | H | H | O | N—CH₃ |
| CN |  | H | Br | H | SCF₂CHFCl | H | Br | O | N—CH₃ |
| CN | ClCH₂ | CH₃ | Cl | H | SCF₃ | H | H | O | N—CH₃ |
| CN | ClCH₂ | CH₃ | Cl | H | OCF₃ | H | Cl | O | S |
| CN | ClCH₃ | C₂H₅ | Br | H | OCF₃ | H | H | O | N—CH₃ |
| CN | ClCH₂ | H | Br | H | OCF₃ | H | Br | O | N—CH₃ |
| CN | CH₃OCH₂ | C₃H₇ | Cl | H | OCF₃ | H | H | O | S |
| CN | CH₃OCH₂ | H | Cl | H | OCF₃ | H | Cl | O | O |
| CN | ClCH₂ | H | Cl | H | SCF₃ | H | H | O | S |
| CN | ClCH₂ | H | Cl | H | SCF₃ | H | Cl | O | N—CH₃ |
| CN | ClCH₂ | H | Br | H | SCF₃ | H | H | O | S |

TABLE 1-continued

| R | R¹ | R² | R³ | R⁴ | R⁵ | R⁶ | R⁷ | X | Y |
|---|---|---|---|---|---|---|---|---|---|
| CN | $CH_3$ | $CH_3$ | Cl | H | $S(O)CF_3$ | H | H | O | S |
| CN | $CH_3$ | $CH_3$ | Cl | H | $S(O)CF_3$ | H | Cl | O | O |
| CN | $CH_3$ | $C_3H_7$ | Br | H | $S(O)CF_3$ | H | Br | O | N—$CH_3$ |
| CN | $CH_3$ | $C_2H_5$ | Br | H | $S(O)CF_3$ | H | H | O | O |
| CN | $CH_3$ | $C_3H_7$ | $CF_3$ | H | $S(O)CF_3$ | H | H | O | O |
| CN | $CH_3$ | H | $CF_3$ | H | $S(O)CF_3$ | H | Cl | O | O |
| CN | $C_2H_5$ | H | Cl | H | $S(O)CF_3$ | H | H | O | O |
| CN | $C_2H_5$ | $CH_3$ | Cl | H | $S(O)CF_3$ | H | Cl | O | S |
| CN | $C_2H_5$ | $CH_3$ | Br | H | $S(O)CF_3$ | H | Br | O | N—$CH_3$ |
| CN | $C_2H_5$ | H | Br | H | $S(O)CF_3$ | H | H | O | O |
| CN | $C_2H_5$ | H | $CF_3$ | H | $S(O)CF_3$ | H | H | O | S |
| CN | $C_2H_5$ | H | $CF_3$ | H | $S(O)CF_3$ | H | Cl | O | O |
| CN | cyclopropyl | H | Cl | H | $S(O)CF_3$ | H | H | O | N—$CH_3$ |
| CN | cyclopropyl | H | Cl | H | $S(O)CF_3$ | H | Cl | O | O |
| CN | cyclopropyl | H | Br | H | $S(O)CF_3$ | H | Br | O | S |
| CN | cyclopropyl | H | Br | H | $S(O)CF_3$ | H | H | O | S |
| CN | cyclopropyl | H | $CF_3$ | H | $S(O)CF_3$ | H | H | O | N—$CH_3$ |
| CN | cyclopropyl | H | $CF_3$ | H | $S(O)CF_3$ | H | Cl | O | O |
| CN | $CH_3$ | H | Cl | H | $OCF_2CHFCl$ | H | H | O | S |
| CN | $CH_3$ | H | Cl | H | $OCF_2CHFCl$ | H | Cl | O | S |
| CN | $CH_3$ | $CH_3$ | Br | H | $OCF_2CHFCl$ | H | H | O | O |
| CN | $CH_3$ | $C_2H_5$ | Br | H | $OCF_2CHFCl$ | H | Br | O | N—$CH_3$ |
| CN | $C_2H_5$ | $C_3H_7$ | Cl | H | $OCF_2CHFCl$ | H | H | O | O |
| CN | $C_2H_5$ | $C_2H_5$ | Cl | H | $OCF_2CHFCl$ | H | Cl | O | S |
| CN | $C_2H_5$ | $CH_3$ | Br | H | $OCF_2CHFCl$ | H | H | O | N—$CH_3$ |
| CN | $C_2H_5$ | H | Br | H | $OCF_2CHFCl$ | H | Br | O | O |
| CN | cyclopropyl | H | Cl | H | $OCF_2CHFCl$ | H | H | O | S |
| CN | cyclopropyl | H | Cl | H | $OCF_2CHFCl$ | H | Cl | O | S |
| CN | cyclopropyl | H | Br | H | $OCF_2CHFCl$ | H | H | N | N—$CH_3$ |
| CN | cyclopropyl | H | Br | H | $OCF_2CHFCl$ | H | Br | O | N—$CH_3$ |
| CN | $CH_3$ | $CH_3$ | Cl | H | $OCF_2CHCl_2$ | H | H | O | O |
| CN | $CH_3$ | $C_2H_5$ | Cl | H | $OCF_2CHCl_2$ | H | Cl | O | O |
| CN | $CH_3$ | $C_3H_7$ | Br | H | $OCF_2CHCl_2$ | H | H | O | O |
| CN | $CH_3$ | H | Br | H | $OCF_2CHCl_2$ | H | Br | O | O |
| CN | $C_2H_5$ | H | Cl | H | $OCF_2CHCl_2$ | H | H | O | O |
| CN | $C_2H_5$ | H | Cl | H | $OCF_2CHCl_2$ | H | Cl | O | S |
| CN | $C_2H_5$ | H | Br | H | $OCF_2CHCl_2$ | H | H | O | N—$CH_3$ |
| CN | $C_2H_5$ | $CH_3$ | Br | H | $OCF_2CHCl_2$ | H | Br | O | O |
| CN | cyclopropyl | $C_2H_5$ | Cl | H | $OCF_2CHCl_2$ | H | H | O | O |
| CN | cyclopropyl | $C_3H_7$ | Cl | H | $OCF_2CHCl_2$ | H | Cl | O | O |

TABLE 1-continued

| R | R¹ | R² | R³ | R⁴ | R⁵ | R⁶ | R⁷ | X | Y |
|---|---|---|---|---|---|---|---|---|---|
| CN | ⊳⊲H | H | Br | H | OCF$_2$CHCl$_2$ | H | H | O | O |
| CN | ⊳⊲H | CH$_3$ | Br | H | OCF$_2$CHCl$_2$ | H | Br | O | S |
| CN | CH$_3$ | C$_2$H$_5$ | Cl | H | OCF$_2$CHF$_2$ | H | H | O | S |
| CN | CH$_3$ | C$_3$H$_7$ | Cl | H | OCF$_2$CHF$_2$ | H | Cl | O | N—CH$_3$ |
| CN | CH$_3$ | H | Br | H | OCF$_2$CHF$_2$ | H | H | O | S |
| CN | CH$_3$ | H | Br | H | OCF$_2$CHF$_2$ | H | Br | O | O |
| CN | C$_2$H$_5$ | H | Cl | H | OCF$_2$CHF$_2$ | H | H | O | N—CH$_3$ |
| CN | C$_2$H$_5$ | H | Cl | H | OCF$_2$CHF$_2$ | H | Cl | O | S |
| CN | C$_2$H$_5$ | H | Br | H | OCF$_2$CHF$_2$ | H | H | O | O |
| CN | C$_2$H$_5$ | H | Br | H | OCF$_2$CHF$_2$ | H | Br | O | S |
| CN | ⊳⊲H | H | Cl | H | OCF$_2$CHF$_2$ | H | H | O | S |
| CN | ⊳⊲H | H | Cl | H | OCF$_2$CHF$_2$ | H | Cl | O | S |
| CN | ⊳⊲H | H | Br | H | OCF$_2$CHF$_2$ | H | H | O | N—CH$_3$ |
| CN | ⊳⊲H | H | Br | H | OCF$_2$CHF$_2$ | H | Br | O | N—CH$_3$ |
| CN | CH$_3$ | H | Cl | H | SO$_2$CH$_3$ | H | H | O | O |
| CN | CH$_3$ | H | Cl | H | SO$_2$CH$_3$ | H | Cl | O | S |
| CN | CH$_3$ | H | Br | H | SO$_2$CH$_3$ | H | H | O | N—CH$_3$ |
| CN | CH$_3$ | CH$_3$ | Br | H | SO$_2$CH$_3$ | H | Br | O | O |
| CN | CH$_3$ | CH$_3$ | CF$_3$ | H | SO$_2$CH$_3$ | H | H | O | S |
| CN | C$_2$H$_5$ | CH$_3$ | Cl | H | SO$_2$CH$_3$ | H | H | O | N—CH$_3$ |
| CN | C$_2$H$_5$ | C$_2$H$_5$ | Cl | H | SO$_2$CH$_3$ | H | Cl | O | O |
| CN | C$_2$H$_5$ | C$_2$H$_5$ | Br | H | SO$_2$CF$_3$ | H | H | O | S |
| CN | C$_2$H$_5$ | C$_2$H$_5$ | Br | H | SO$_2$CF$_3$ | H | Br | O | O |
| CN | C$_2$H$_5$ | CH$_3$ | CF$_3$ | H | SO$_2$CF$_3$ | H | H | O | N—CH$_3$ |
| CN | ⊳⊲H | CH$_3$ | Cl | H | SO$_2$CF$_3$ | H | H | O | S |
| CN | ⊳⊲H | CH$_3$ | Cl | H | SO$_2$CF$_3$ | H | Cl | O | O |
| CN | ⊳⊲H | H | Br | H | SO$_2$CF$_3$ | H | H | O | N—CH$_3$ |
| CN | ⊳⊲H | H | Br | H | SO$_2$CF$_3$ | H | Br | O | S |
| CN | ⊳⊲H | H | CF$_3$ | H | SO$_2$CF$_3$ | H | H | O | O |
| CN | CH$_3$ | H | F | H | SCCl$_2$F | H | H | O | O |
| CN | CH$_3$ | H | F | H | SCCl$_2$F | H | F | O | S |
| CN | CH$_3$ | H | F | F | SCCl$_2$F | F | F | O | N—CH$_3$ |
| CN | CH$_3$ | CH$_3$ | Cl | H | SCCl$_2$F | H | H | O | O |
| CN | CH$_3$ | CH$_3$ | Cl | H | SCCl$_2$F | H | Cl | O | S |
| CN | CH$_3$ | CH$_3$ | Cl | H | SCCl$_2$F | H | F | O | N—CH$_3$ |
| CN | CH$_3$ | C$_2$H$_5$ | Br | H | SCCl$_2$F | H | H | O | O |
| CN | CH$_3$ | C$_2$H$_5$ | Br | H | SCCl$_2$F | H | Br | O | S |
| CN | C$_2$H$_5$ | C$_2$H$_5$ | F | H | SCCl$_2$F | H | H | O | S |
| CN | C$_2$H$_5$ | C$_2$H$_5$ | F | H | SCCl$_2$F | H | F | O | O |
| CN | C$_2$H$_5$ | C$_2$H$_5$ | F | H | SCCl$_2$F | F | F | O | N—CH$_3$ |
| CN | C$_2$H$_5$ | CH$_3$ | Cl | H | SCCl$_2$F | H | H | O | S |
| CN | C$_2$H$_5$ | CH$_3$ | Cl | H | SCCl$_2$F | H | Cl | O | O |
| CN | C$_2$H$_5$ | H | Cl | H | SCCl$_2$F | H | F | O | N—CH$_3$ |
| CN | C$_2$H$_5$ | H | Br | H | SCCl$_2$F | H | H | O | S |
| CN | C$_2$H$_5$ | H | Br | H | SCCl$_2$F | H | Br | O | O |

TABLE 1-continued

| R | R¹ | R² | R³ | R⁴ | R⁵ | R⁶ | R⁷ | X | Y |
|---|---|---|---|---|---|---|---|---|---|
| CN | ▷−H (cyclopropyl) | H | F | H | SCCl₂F | H | H | O | S |
| CN | ▷−H | H | F | H | SCCl₂F | H | F | O | N—CH₃ |
| CN | ▷−H | CH₃ | F | F | SCCl₂F | F | F | O | O |
| CN | ▷−H | CH₃ | Cl | H | SCCl₂F | H | H | O | S |
| CN | ▷−H | CH₃ | Cl | H | SCCl₂F | H | Cl | O | N—CH₃ |
| CN | ▷−H | C₂H₅ | Cl | H | SCCl₂F | H | F | O | O |
| CN | ▷−H | C₂H₅ | Br | H | SCCl₂F | H | H | O | S |
| CN | ▷−H | C₂H₅ | Br | H | SCCl₂F | H | Br | O | N—CH₃ |
| CN | CH₃ | H | F | H | OCHF₂ | H | H | O | O |
| CN | CH₃ | H | F | H | OCHF₂ | H | F | O | S |
| CN | CH₃ | H | F | F | OCHF₂ | F | F | O | N—CH₃ |
| CN | CH₃ | H | Cl | H | OCHF₂ | H | H | O | O |
| CN | CH₃ | H | Cl | H | OCHF₂ | H | Cl | O | O |
| CN | CH₃ | H | Cl | H | OCHF₂ | H | F | O | O |
| CN | CH₃ | H | Br | H | OCHF₂ | H | H | O | S |
| CN | CH₃ | H | Br | H | OCHF₂ | H | Br | O | S |
| CN | C₂H₅ | H | F | H | OCHF₂ | H | H | O | S |
| CN | C₂H₅ | H | F | H | OCHF₂ | H | F | O | S |
| CN | C₂H₅ | H | F | F | OCHF₂ | F | F | O | N—CH₃ |
| CN | C₂H₅ | H | Cl | H | OCHF₂ | H | H | O | N—CH₃ |
| CN | C₂H₅ | H | Cl | H | OCHF₂ | H | Cl | O | N—CH₃ |
| CN | C₂H₅ | H | Cl | H | OCHF₂ | H | F | O | N—CH₃ |
| CN | C₂H₅ | H | Br | H | OCHF₂ | H | F | O | O |
| CN | C₂H₅ | H | Br | H | OCHF₂ | H | Br | O | O |
| CN | ▷−H | H | F | H | OCHF₂ | H | H | O | O |
| CN | ▷−H | H | F | H | OCHF₂ | H | F | O | S |
| CN | ▷−H | H | F | F | OCHF₂ | F | F | O | O |
| CN | ▷−H | CH₃ | Cl | H | OCHF₂ | H | H | O | O |
| CN | ▷−H | CH₃ | Cl | H | OCHF₂ | H | Cl | O | O |
| CN | ▷−H | CH₃ | Cl | H | OCH₂F | H | F | O | O |
| CN | ▷−H | C₂H₅ | Br | H | OCH₂F | H | H | O | O |
| CN | ▷−H | C₂H₅ | Br | H | OCHF₂ | H | Br | O | O |

TABLE 1-continued

| R | R¹ | R² | R³ | R⁴ | R⁵ | R⁶ | R⁷ | X | Y |
|---|---|---|---|---|---|---|---|---|---|
| CN | 2,2-dichloro-1-methylcyclopropyl | $C_2H_5$ | Cl | H | $OCF_3$ | H | H | O | $N-CH_3$ |
| CN | 2,2-dichloro-1-methylcyclopropyl | $C_2H_5$ | Cl | H | $OCF_3$ | H | Cl | O | $N-CH_3$ |
| CN | 2,2-dichloro-1-methylcyclopropyl | $C_2H_5$ | Cl | H | $SCF_3$ | H | H | O | $N-CH_3$ |
| CN | 2,2-dichloro-1-methylcyclopropyl | $C_3H_7$ | Cl | H | $SCF_3$ | H | Cl | O | $N-CH_3$ |
| CN | 2,2-dichloro-1-methylcyclopropyl | $C_3H_7$ | Cl | H | $SO_2CF_3$ | H | H | O | $N-CH_3$ |
| CN | 2,2-dichloro-1-methylcyclopropyl | H | Cl | H | $SO_2CF_3$ | H | Cl | O | $N-C_2H_5$ |
| CN | phenyl | H | Cl | H | $OCF_3$ | H | Cl | O | $N-C_2H_5$ |
| CN | phenyl | H | Cl | H | $SCF_3$ | H | Cl | O | $N-C_3H_7$ |
| CN | 4-Cl-phenyl | H | Cl | H | $OCF_3$ | H | Cl | O | $N-CH=CH_2$ |
| CN | 4-Cl-phenyl | H | Cl | H | $SCF_3$ | H | Cl | O | $N-C_3H_7$ |
| CN | 4-$CH_3$-phenyl | H | Cl | H | $OCF_3$ | H | Cl | O | $N-C_2H_5$ |
| CN | 4-$CH_3$-phenyl | H | Cl | H | $SCF_3$ | H | Cl | O | $N-CH_3$ |
| CN | 4-$O_2N$-phenyl | H | Cl | H | $OCF_3$ | H | Cl | O | $N-C_2H_5$ |

TABLE 1-continued

| R | R$^1$ | R$^2$ | R$^3$ | R$^4$ | R$^5$ | R$^6$ | R$^7$ | X | Y |
|---|---|---|---|---|---|---|---|---|---|
| CN | 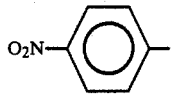 | H | Cl | H | SCF$_3$ | H | Cl | O | N—C$_3$H$_7$ |

If, for example, 5-amino-4-cyano-1-(2',6'-dichloro-4'-trifluoromethylthiophenyl)-pyrazole and phenyl chloroformate are used as starting materials, the course of the reaction of process (a-α) according to the invention can be represented by the following equation:

If, for example, 4-cyano-5-(bisphenoxycarbonylamino)-1-(2',6'-dichloro-4'-trifluoromethylthiophenyl)pyrazole and methanol are used as starting materials, the course of the reaction of process (b) according to the invention can be represented by the following equation:

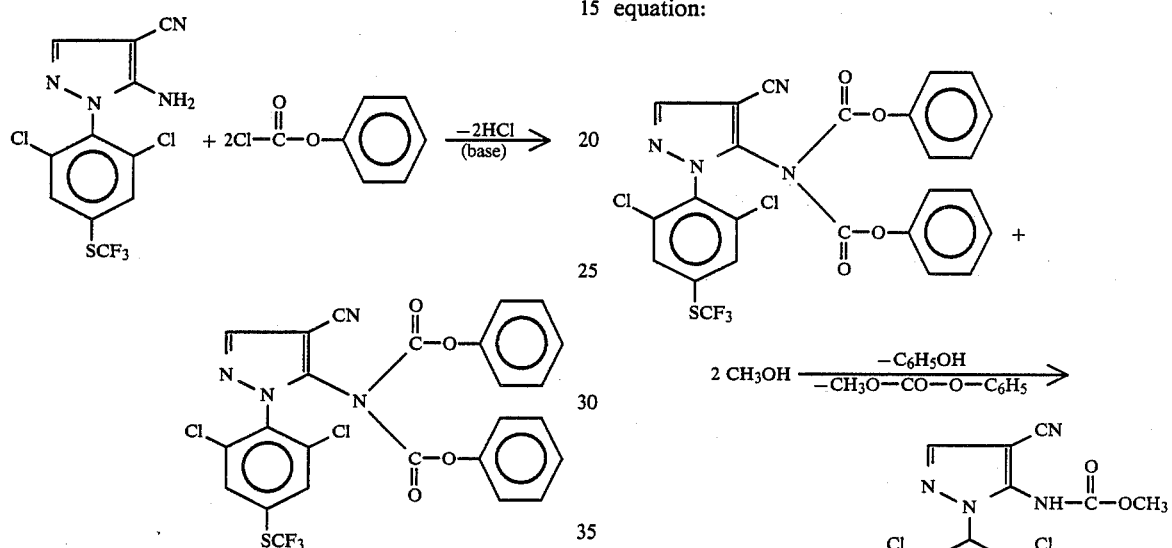

If, for example, 5-amino-4-methoxycarbonyl-1-(2',6'-dichloro-4-trifluoromethoxyphenyl)-pyrazole and methyl isocyanate are used as starting materials, the course of the reaction of process (a-β) according to the invention can be represented by the following equation:

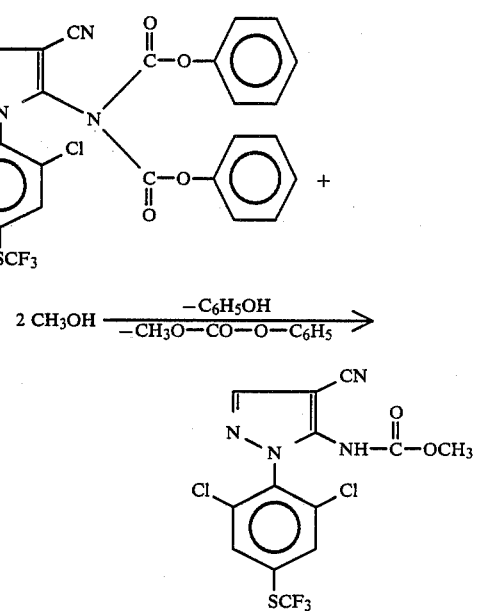

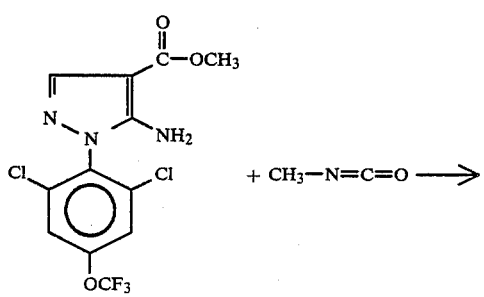

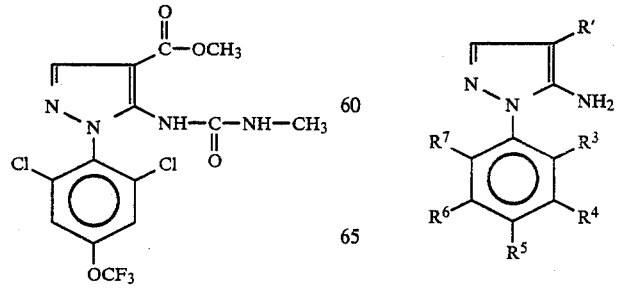

Formula (II) gives a general definition of the 5-aminopyrazoles required as starting materials for carrying out process (a/α and β) according to the invention. In this formula (II), R, R$^3$, R$^4$, R$^5$, R$^6$ and R$^7$ preferably have the meaning which have already been mentioned in the description of the substances according to the invention, of the formula (I) as being preferred for these substituents.

Some of the 5-aminopyrazoles of the folmula (II) are known (see, for example, European Patent No. 34,945; DE-OS (German Published Specification) No. 3,226,496 and DE-OS (German Published Specification) No. 3,129,429).

5-Aminopyrazoles of the formula (IIa),

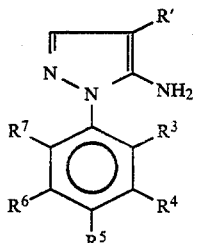

(IIa)

in which

R' represents alkoxycarbonyl, alkenyloxycarbonyl, alkinyloxycarbonyl, alkenylaminocarbonyl or alkinylaminocarbonyl and $R^3$, $R^4$, $R^5$, $R^6$ and $R^7$ have the meaning given above form the subject of U.S. application Ser. No. 659,731, filed Oct. 11, 1984, now pending, corresponding to (German DE-P No. 33 37 543.7 filed Oct. 15, 1983).

They are obtained by processes which are known in principle, when acrylonitrile derivatives of the formula (VIa)

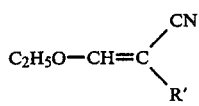 (VIa)

in which

R' has the meaning given above, are reacted with phenylhydrazines of the formula (VII)

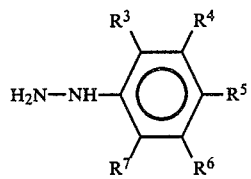 (VII)

in which $R^3$, $R^4$, $R^5$, $R^6$ and $R^7$ have the meaning given above, either the reaction first being carried out in a first stage, if appropriate in the presence of a diluent, such as, for example, glacial acetic acid or ethanol, and, if appropriate, in the presence of a reaction auxiliary, such as, for example, sodium acetate, at temperatures between $-20°$ C. and $+20°$ C., to give the phenylhydrazine derivatives of the formula (VIIIa)

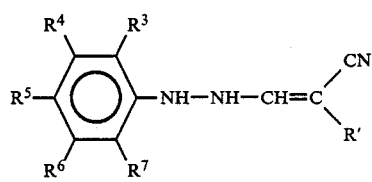 (VIIIa)

in which

R', $R^3$, $R^4$, $R^5$, $R^6$ and $R^7$ have the meaning given above, and these being cyclized in a second stage, if appropriate in the presence of a diluent, such as, for example, ethylene glycol monethyl ether at temperatures between $+50°$ C. and $+150°$ C., or cyclization being carried out directly in one reaction step, without isolation of the intermediate of the formula (VIIIa), if appropriate in the presence of a diluent, such as, for example, ethylene glycol monoethyl ether or ethanol, at temperatures between $+50°$ and $+150°$ C.

5-Aminopyrazoles of the formula (IIb),

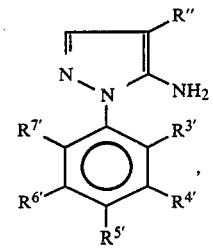 (IIb)

in which

R" represents cyano or alkylaminocarbonyl and $R^{3'}$, $R^{4'}$, $R^{5'}$, $R^{6'}$ and $R^{7'}$, which are identical or different, represent hydrogen, halogen, cyano, nitro, alkyl, alkoxy, alkylsulphonyl, alkoxycarbonyl or the radical $-X'-R^8$, wherein X' represents oxygen, sulphur, sulphinyl or sulphonyl and $R^8$ represents halogenoalkyl, with the proviso that at least one of the radicals $R^{3'}$, $R^{4'}$, $R^{5'}$, $R^{6'}$ or $R^{7'}$ represents a radical $-X'-R^8$, and X' does not represent oxygen when $R^8$ represents trifluoromethyl are obtained by processes which are known in principle, in a manner analogous to the 5-aminopyrazoles of the formula (IIa), when acrylonitrile derivatives of the formula (VIb)

 (VIb)

in which

R" has the meaning given above, are reacted with phenylhydrazines of the formula (VIIa)

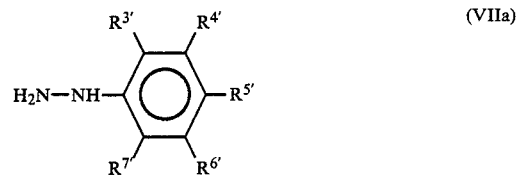 (VIIa)

in which $R^{3'}$, $R^{4'}$, $R^{5'}$, $R^{6'}$ and $R^{7'}$ have the meaning given above, either the reaction first being carried out in a first stage, if appropriate in the presence of a diluent, such as, for example, glacial acetic acid or ethanol, and, if appropriate, in the presence of a reaction auxiliary, such as, for example, sodium acetate, at temperatures between $-20°$ C. and $+20°$ C., to give the phenyl hydrazine derivatives of the formula (VIIIb)

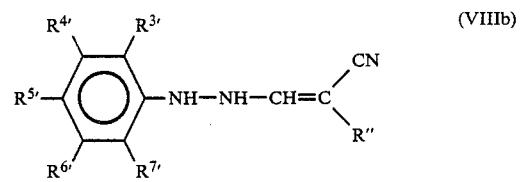 (VIIIb)

in which

R'', R³', R⁴', R⁵', R⁶' and R⁷' have the meaning given above, and these being cyclized in a 2nd stage, if appropriate in the presence of a diluent, such as, for example, ethylene glycol monoethyl ether, at temperatures between +50° C. and +150° C., or cyclization being carried out directly in one reaction step, without isolation of the intermediate of the formula (VIIIb), if appropriate in the presence of a diluent, such as, for example, ethylene glycol monoethyl ether or ethanol, at temperatures between +50° C. and +150° C.

The compounds of the formulae (IIb), (VIIIa) and (VIIIb) likewise form the subject of the abovementioned U.S. application Ser. No. 659,731, filed Oct. 11, 1984, now pending, corresponding to German Application No. DE-P33 37 543.7.

The acrylonitrile derivatives of the formulae (VIa) and (VIb) are known (see, for example, European Pat. No. 34,945 or DE-OS (German Published Specification No. 3,129,429).

The majority of the phenylhydrazines of the formulae (VII) and (VIIa) are known or can be prepared in a simple, analogous manner, by known processes (see, for example, Houben-Weyl, "Methoden der organischen Chemie" [Methods of organic chemistry] Volume X/2, page 203, Thieme Verlag Stuttgart 1967), by reacting, for example, the known anilines of the formula (IX)

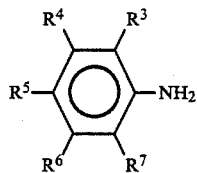

in which

R³, R⁴, R⁵, R⁶ and R⁷ have the meaning given above, with sodium nitrite in the presence of an acid, such as, for example, sulphuric acid, and then with tin(II) chloride, likewise in the presence of an acid, such as, for example, hydrochloric acid, at temperatures between −20° C. and +80° C.

Formula (III) gives a general definition of the acylating agents furthermore required as starting materials for carrying out process (a-α) according to the invention. In this formula (III), R¹, X and Y preferably represent those radicals which have already been mentioned in the description of the substances according to the invention, of the formula (I), as being preferred for these substituents. A preferably represents halogen, in particular chlorine or bromine. The acylating agents of the formula (III) are generally known compounds of organic chemistry.

Formula (IV) gives a general definition of the iso(thio)cyanates furthermore required as starting materials for carrying out process (a-β) according to the invention. In this formula (IV), R¹ and X preferably represent those radicals which have already been mentioned in the description of the substances according to the invention, of the formula (I), as being preferred for these substituents.

The iso(thio)cyanates of the formula (IV) are likewise generally known compounds of organic chemistry.

Formula (Ia) gives a general definition of the biscarbamates required as starting materials for carrying out process (b) according to the invention. In this formula (Ia), R, R³, R⁴, R⁵, R⁶ and R⁷ preferably represent those radicals which have already been mentioned in the description of the substances according to the invention, of the formula (I), for these substituents. Ar preferably represents phenyl which is optionally monosubstituted to trisubstituted by identical or different substituents from amongst halogen, cyano, nitro, methyl, ethyl, methoxy, ethoxy and trifluoromethyl.

The biscarbamates of the formula (Ia) are compounds according to the invention and are obtainable by process (a-α).

Formula (V) gives a general definition of the alcohols, amines or thiols furthermore required as starting materials for carrying out process (b) according to the invention. In this formula (V), R¹ and Y preferably represent those radicals which have already been mentioned in the description of the substances according to the invention, of the formula (I), as being preferred for these substituents.

The alcohols, amines and thiols of the formula (V) are generally known compounds of organic chemistry.

Suitable diluents for carrying out processes (a/α+β) according to the invention are inert organic solvents. Aliphatic or aromatic, optionally halogenated hydrocarbons, such as benzine, benzene, toluene, xylene, pentane, hexane, heptane, cyclohexane, petroleum ether, ligroin, methylene chloride, ethylene chloride, chloroform, carbon tetrachloride, chlorobenzene or dichlorobenzene, ethers, such as diethyl ether or diisopropyl ether, ethylene glycol dimethyl ether, tetrahydrofuran or dioxane, ketones, such as acetone or butanone, methyl isopropyl ketone or methyl isobutyl ketone, esters, such ethyl acetate, nitriles, such as acetonitrile or proprionitrile, and amides, such as dimethylformamide, dimethylacetamide, N-methylpyrrolidone or hexamethylphosphoric acid triamide, are preferably used.

If acylating agents of the formula (III) are used in liquid form, it is also possible to employ these in appropriate excess as a diluent.

Suitable acid-binding agents or catalysts for the processes (a/α+β) according to the invention are all inorganic and organic bases which can customarily be used. Alkali metal hydroxides or carbonates, such as, for example, sodium hydroxide, potassium hydroxide, sodium carbonate or potassium carbonate, or tertiary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU), are preferably used.

In the processes (a/α+β) according to the invention, the reaction temperatures can be varied within a wide range. In general, the reactions are carried out at between −20° C. and +150° C., preferably between 0° C. and +100° C.

To carry out process (a) according to the invention, in general 1 to 20 mols, preferably 1 to 15 mols, of the acylating agent of the formula (III) or the iso(thio)cyanate of the formula (IV) and, if appropriate, in general 1 to 3 mols, preferably 1 to 2 mols, of the acid-binding agent are employed per mol of 5-aminopyrazole of the formula (II). The reaction procedure, the working up and the isolation of the end products of the formula (I) are carried out in a customary manner.

Suitable diluents for carrying out process (b) according to the invention are likewise inert organic solvents. Preferably used solvents are the organic solvents mentioned in the case of process (a), or alcohols, such as methanol, ethanol or isopropanol.

However, it is also possible for the alcohols, amines or thiols of the formula (V) which are used as reactants to be employed in an appropriate excess and to serve simultaneously as diluents.

In process (b) according to the invention, the reaction temperatures can likewise be varied within a wide range. In general, the reaction is carried out at between 0° C. and +200° C., preferably between +20° C. and +150° C.

To carry out process (b) according to the invention, in general 1 to 20 mols, preferably 1 to 10 mols, of the alcohol or amine or thiol of the formula (V) are employed per mol of the biscarbamate of the formula (Ia), and the mixture is heated to the required temperature for several hours. The working up and isolation of the reaction products of the formula (I) are carried out by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforrestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention, of the formula (I), exhibit not only a particularly good general herbicidal activity but also a substantially improved selectivity, with respect to crop plants, in important crops, such as, for example, wheat. The precursors of the formula (II) as well as the precursers of the formulae (VIIIa) and (VIIIb) likewise possess herbicidal activity and pronounced selectivity with respect to important crop plants.

The active compounds can be converted to the customary formulations, such as solutions, emulsisons, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixing being possible.

Possible components for the mixtures are known herbicides, for example benzonitriles, diphenyl ether, pyridoxy-phenoxypropionic acids, phenoxyalkanecarboxylic acids, ureas, triazinones or triazinediones, such as, for example, 3,5-dibromo- or 3,5-diiodo-4-hydroxybenzonitrile, 2-benzyloxyethyl, 2,2-diethoxyethyl or trimethylsilylmethyl α-[4-(3,5-dichloro-2-pyridoxy)-phenoxy]-propionate, 2,4-dichlorophenoxyacetic acid, α-(2,4-dichlorophenoxy)propionic acid, 4-chloro-2-methylphenoxy-acetic acid, α-(4-chloro-2-methyl-phenoxy)-propionic acid, 1-amino-6-ethylthio-3-(2,2-dimethylpropyl)-1,3,5-triazine-2,4-(1H,3H)dione or N-(2-benzothiazolyl)-N,N'-dimethyl-urea for combating weeds in cereals; 4-amino-3-methyl-6-phenyl-1,2,4-triazin-5(4H)-one for combating weeds in sugar beets, and 4-amino-6-(1,1-dimethylethyl)-3-methylthio- or 3-ethylthio-1,2,4-triazin-5(4H)-one for combating weeds in soy beans. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and the use of the active compounds according to the invention can be seen from the following examples.

Preparation examples

EXAMPLE 1

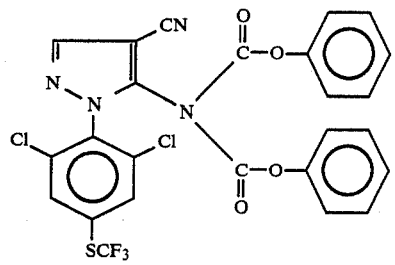

(Process a-α)

First 52.2 g (0.3 mol) of phenyl chloroformate and then 23.7 g (0.3 mol) of pyridine in 30 ml of chloroform are added dropwise to 35.3 g (0.1 mol) of 5-amino-4-cyano-1-(2,6-dichloro-4-trifluoromethylthiophenyl)-pyrazole in 100 ml of chloroform at 0° C. to 5° C., while stirring and cooling with ice. When the addition is complete, stirring is continued for a further 16 hours at room temperature, the solid is filtered off under suction and rinsed with chloroform, and the residue is stirred with water. The crystalline product is filtered off under suction, dried, and recrystallized from toluene. 46 g (78% of theory) of 4-cyano-5-(N,N-bisphenoxycarbonylamino)-1-(2,6-dichloro-4-trifluoromethylthio)-pyrazole of melting point 164° to 167° C. are obtained.

EXAMPLE 2

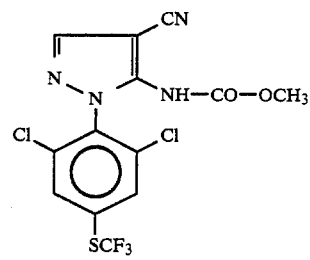

(Process b)

18.2 g (0.02 mol) of 4-cyano-5-(N,N-bisphenoxycarbonylamino)-1-(2,6-dichloro-4-trifluoromethylthio)-pyrazole in 200 ml (160 g, 5 mol) of anhydrous methanol are heated to the boil, and boiled under reflux until a clear solution is formed. The excess methanol is distilled off, the residue is taken up in chloroform, the solution is washed with aqueous sodium bicarbonate solution, dried over sodium sulphate and evaporated down, and the residue is recrystallized from toluene. 5.8 g (71% of theory) of 4-cyano-1-(2,6-dichloro-4-trifluoromethylthio-phenyl)-5-methoxycarbonylamino-pyrazole of melting point 145° C. are obtained.

The following substituted 5-acylamino-1-phenyl-pyrazoles of the formula (I) are obtained in a corresponding manner and according to the general preparation information:

TABLE 2

Structure (I):

$$\text{Pyrazole-N-N(R^2)-C(=X)-Y-R^1 with substituted phenyl (R^3,R^4,R^5,R^6,R^7)}$$

| Example No. | R | R¹ | R² | R³ | R⁴ | R⁵ | R⁶ | R⁷ | X | Y | Melting Point (°C.) |
|---|---|---|---|---|---|---|---|---|---|---|---|
| 3 | CN | CH₃ | H | Cl | H | —OCF₃ | H | H | O | O | 122 |
| 4 | CN | CH₃ | H | Cl | H | —OCF₃ | H | H | O | —N(CH₃)— | 140 |
| 5 | CN | C₆H₅ | C₆H₅—O—C— | Cl | H | —OCF₃ | H | H | O | O | 155–157 |
| 6 | CN | C₂H₅ | H | Cl | H | —OCF₃ | H | H | O | O | 90 |
| 7 | CN | C₆H₅ | C₆H₅—O—C— | Cl | H | —OCF₃ | H | Cl | O | O | 150 |
| 8 | CN | CH₃ | H | Cl | H | —OCF₃ | H | Cl | O | O | 108–110 |
| 9 | CN | C₆H₅ | C₆H₅—O—C— | Cl | H | CF₃SO₂— | H | Cl | O | O | 155–157 |
| 10 | CN | CH₃ | H | Cl | H | CF₃SO₂— | H | Cl | O | —N(CH₃)— | 189–190 |
| 11 | CN | CH₃ | H | Cl | H | —OCF₃ | H | Cl | O | —N(CH₃)— | 172–174 |
| 12 | CN | CH₃ | H | Cl | H | CF₃SO₂— | H | Cl | O | O | 198–200 |
| 13 | CN | CH₃ | H | Cl | H | —SCF₃ | H | Cl | O | —N(CH₃)— | 198–199 |
| 14 | CN | CH₃ | H | Cl | H | CF₃ | H | Cl | O | —N(CH₃)— | 224–225 |
| 15 | CN | C₂H₅ | H | Cl | H | —SO₂CF₃ | H | Cl | O | O | 182 |
| 16 | CN | nC₄H₉ | H | Cl | H | —SO₂CF₃ | H | Cl | O | S | 147 |

Preparation of the starting materials:

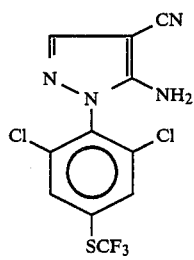

(II-1)

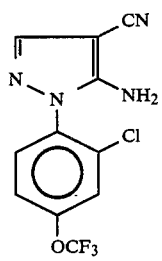

(II-2)

14.1 g (0.04 mol) of 1-(2,2-dicyanoethen-1-yl)-2-(2,6-dichloro-4-trifluoromethylthio-phenyl)-hydrazine in 30 ml of ethylene glycol monoethyl ether are heated under reflux for 2 hours. Active carbon is added to the hot solution, the mixture is filtered and the filtrate is diluted with 60 ml of water. This precipitate which separtes out is filtered off under suction and dried. 9.8 g (70% of theory) of 5-amino-4-cyano-1-(2,6-dichloro-4-trifluoromethylthiophenyl)-pyrazole of melting point 185° C. to 187° C. are obtained.

3.08 g (0.025 mol) of ethoxymethylenemalonodinitrile and 5.7 g (0.025 mol) of 2-chloro-4-trifluoromethoxyphenylhydrazine in 50 ml of ethylene glycol monoethyl ether are heated under reflux for 3 hours, cooled and then poured onto water, the crystalline precipitate is filtered off under suction and stirred with petroleum ether, the mixture is cooled and the product is again filtered off under suction. 5.3 g (73.6% of theory) of 5-amino-4-cyano-1-(2-chloro-4-trifluoromethoxyphenyl)-pyrazole of melting point of 115° C. are obtained.

The following new 5-amino-pyrazoles of the formula (II) are obtained in a corresponding manner and according to the general preparation information:

TABLE 3

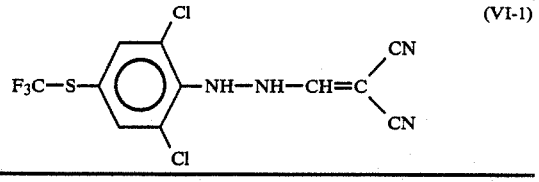

| Example No. | R | $R^3$ | $R^4$ | $R^5$ | $R^6$ | $R^7$ | Melting point (°C.) |
|---|---|---|---|---|---|---|---|
| II-3 | $C_2H_5OCO-$ | Cl | H | $-CF_3$ | H | Cl | 134–135 |
| II-4 | $C_2H_5OCO-$ | Cl | H | $-CF_3$ | H | H | 112–114 |
| II-5 | $C_2H_5OCO-$ | Cl | H | $-OCF_3$ | H | H | 115–118 |
| II-6 | $C_2H_5OCO-$ | Cl | H | $-OCF_3$ | H | Cl | 153–154 |
| II-7 | CN | Cl | H | $-SCF_3$ | H | H | 159 |
| II-8 | CN | H | Cl | $-SCF_3$ | H | H | 126–128 |
| II-9 | CN | H | H | $-SCF_3$ | H | H | 122 |
| II-10 | $C_2H_5OCO-$ | H | Cl | $-SCF_3$ | H | H | 120–122 |
| II-11 | $C_2H_5OCO-$ | Cl | H | $-SCF_3$ | H | H | 129–130 |

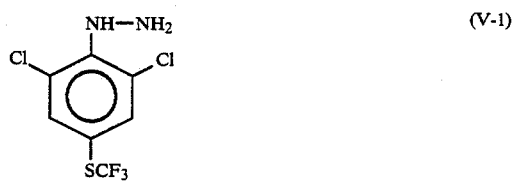

6.1 g (0.05 mol) of ethoxymethylenemalonodinitrile are added to a stirred suspension of 13.9 g (0.05 mol) of (2,6-dichloro-4-trifluoromethylthio)-phenylhydrazine and 2.1 g (0.025 mol) of sodium acetate in 25 ml of glacial acetic acid. When the additon is complete, the mixture is stirred for a further hour at room temperature and the solid thus obtained is filtered off, washed in succession with water, aqueous sodium bicarbonate solution and again with water and then dried. 15.8 g (89% of theory) of 1-(2,2-dicyanoethen-1-yl)-2-(2,6-trichloro-4-trifluoromethylthiophenyl)-hydrazine of melting point 160° C. are obtained.

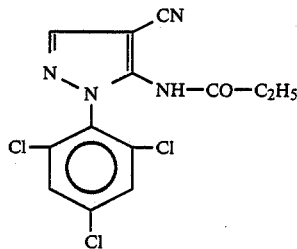

16.6 g (0.24 mol) of sodium nitrite in 150 ml of concentrated sulphuric acid are first added to 50 g (0.2 mol) of 2,6-dichloro-4-trifluoromethylthio-aniline in 435 ml of glacial acetic acid at 55° C. to 60° C., after which 180.5 g (0.8 mol) of tin(II) chloride dihydrate in 188 ml of concentrated hydrochloric acid are added at 5° C. to 10° C. The precipitate thus obtained is filtered off under suction, stirred in 650 ml of a mixture of ice and aqueous ammonia solution, filtered off under suction, dried, and boiled thoroughly twice, each time with one liter of chloroform, the mixtured is filtered and the filtrate is freed from solvent in vacuo. 33 g (62.4% of theory) of (2,6-dichloro-4-trifluoromethylthio)-phenylhydrazine of melting point 58° C. are obtained.

The following new intermediate products of the formula (V) are obtained in a corresponding manner and according to the general preparation information:

TABLE 4

| Example No. | $R^3$ | $R^4$ | $R^5$ | $R^6$ | $R^7$ | Melting point (°C.) |
|---|---|---|---|---|---|---|
| V-2 | Cl | H | $-OCF_3$ | H | H | 35 |
| V-3 | Cl | H | $-OCF_3$ | H | Cl | 61 |
| V-4 | H | Cl | $-OCF_3$ | H | H | 41–42 |
| V-5 | H | H | $-OCF_3$ | H | H | Oil, $n_D^{20} = 1.4799$ |
| V-6 | H | H | $-SCF_3$ | H | H | 55 |
| V-7 | H | Cl | $-SCF_3$ | H | H | 72 |
| V-8 | Cl | H | $-SCF_3$ | H | H | 83 |

USE EXAMPLES

In the use examples below, the compound shown below is employed as a comparative substance:

4-Cyano-5-propionylamino-1-(2,4,6-trichlorophenyl)-pyrazole (disclosed in DE-OS (German Published Specification) No. 3,226,513).

EXAMPLE A

Pre-emergence test

Solvent: 5 parts by weight of acetone
Emulsifier: 1 part by weight of alkylaryl polyglocol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this example, a clearly superior herbicidal activity, as well as a clearly superior selectivity with respect to useful plants, compared with the prior art, is shown, for example, by the compound according to preparation Example (3); this applies particularly to wheat.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this example, a clearly superior herbicidal activity, as well as a clearly superior selectivity with respect to useful plants, compared with the prior art, is shown, for example, by the compound according to preparation Example (2). This likewise applies particularly to wheat.

It will be understood that the specification and examples are illustrated but not limitative of the present invention and that other embodiments within the spirit and scope of the invention will suggest themselves to those skilled in the art.

We claim:

1. A 5-acylamino-1-phenylpyrazole of the formula

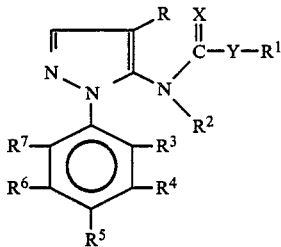

in which
R is cyano or aminocarbonyl, or alkoxycarbonyl, alkenyloxycarbonyl, alkinyloxycarbonyl, alkylaminocarbonyl, alkenylaminocarbonyl or alkinylaminocarbonyl, each of which has up to 4 carbon atoms in the individual alkyl, alkenyl or alkinyl parts,
$R^1$ is alkyl, alkenyl, alkinyl, alkoxyalkyl or alkylthioalkyl each of which has up to 6 carbon atoms in the individual alkyl or alkenyl or alkinyl parts, or is halogenoalkyl having 1 to 6 carbon atoms and 1 to 9 identical or different halogen atoms or is cycloalkyl having 3 to 7 carbon atoms, or aryl which has 6 to 10 carbon atoms and is optionally substituted by halogen, cyano, nitro, and/or alkyl, alkoxy, alkylthio or alkoxycarbonyl, each of which has up to 4 carbon atoms in the individual alkyl parts, or in the case in which Y represents the

group, also may be hydrogen,
X represents oxygen or sulfur,
Y represents oxygen, sulfur or the

group,
Z is hydrogen or alkyl, alkoxy, alkenyl or alkinyl, each of which has up to 4 carbon atoms, or is aryl which has 6 to 10 carbon atoms and is optionally substituted by those substituents mentioned in the case of $R^1$,
$R^2$ is hydrogen or the radical

and
$R^3$, $R^4$, $R^5$, $R^6$ and $R^7$ each independently is hydrogen, fluorine, chlorine, bromine, iodine or nitro, or alkyl, alkoxy, alkylsulphonyl or alkoxycarbonyl, each of which has up to 4 carbon atoms in the particular alkyl parts, or is $-(X')_n-R^8$,
$X'$ is oxygen, sulphur, sulphinyl or sulphonyl,
n is 0 or 1, and
$R^8$ is halogenoalkyl having up to 4 carbon atoms and up to 9 halogen atoms,
with the provisos that
(1) at least one of $R^3$, $R^4$, $R^5$, $R^6$ and $R^7$ is $-(X')_n-R^8$,
(2) when R is aminocarbonyl or alkoxycarbonyl and Y is oxygen, then $R^5$ is not haloalkyl, and
(3) when R is cyano and Y is oxygen, then n is 1.

2. A compound according to claim 1, in which
R is cyano, methoxycarbonyl, ethoxycarbonyl, allyloxycarbonyl, propargyloxycarbonyl, aminocarbonyl, methylaminocarbonyl, dimethylaminocarbonyl, ethylaminocarbonyl, diethylaminocarbonyl, diallylaminocarbonyl or dipropargylaminocarbonyl,
$R^1$ is methyl, ethyl, n- or i-propyl, n-, i-, s- or t-butyl, cyclopropyl, 2,2-dichlorocyclopropyl, 2,2-dichloro-1-methylcyclopropyl, methylthiomethyl, cyclopentyl, cyclohexyl, ethoxymethyl, methoxymethyl, ethoxyethyl, chloromethyl, dichloromethyl, trichloromethyl, trifluoromethyl, dichlorofluoromethyl, difluorochloromethyl or pentafluoroethyl, or is phenyl which is optionally monosubstituted to trisubstituted by fluorine, chlorine, bromine, nitro, methyl and/or methoxy, or, in the case in which Y is

also may be hydrogen,
Z is hydrogen, methyl, ethyl, n- or i-propyl, n-, i-, s- or t-butyl, methoxy, ethoxy, allyl or propargyl, or is phenyl which is optionally monosubstituted to trisubstituted by those substituents mentioned in the case of R¹, R² is hydrogen or the radical

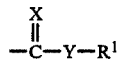

and R³, R⁴, R⁵, R⁶ and R⁷ each independently is hydrogen, fluorine, chlorine, bromine, cyano, nitro, methyl, ethyl, n- or i-propyl, methoxy, ethoxy, methylsulphonyl, methoxycarbonyl, ethoxycarbonyl or a radical —(X')$_n$—R⁸, X' is oxygen, sulphur, sulphinyl or sulphonyl, n is 0 or 1, and R⁸ is trifluoromethyl, trichloromethyl, dichlorofluoromethyl, difluorochloromethyl, dichloromethyl, chloromethyl, difluoromethyl, pentafluoroethyl, tetrafluoroethyl, trifluorochloroethyl, trifluoroethyl, difluorodichloroethyl, trifluorodichloroethyl or pentachloroethyl.

3. A compound according to claim 1, wherein such compound is 4-cyano-1-(2,6-dichloro-4-trifluoromethylthiophenyl)-5-methoxycarbonylamino-pyrazole of the formula

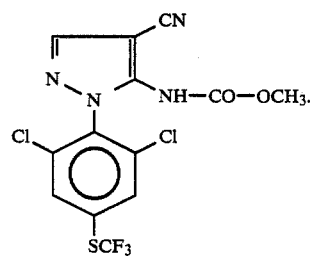

4. A compound according to claim 1, wherein such compound is 1-(2-chloro-4-trifluoromethoxy-phenyl)-4-cyano-5-methoxycarbonylamino-pyrazole of the formula

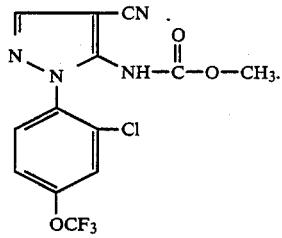

5. A compound according to claim 1, wherein such compound is 1-(2-chloro-4-trifluoromethoxy-phenyl)-4-cyano-5-ethoxycarbonylamino-pyrazole of the formula

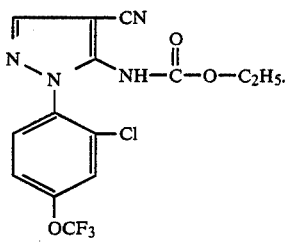

6. A compound according to claim 1, wherein such compound is 4-cyano-1-(2,6-dichloro-4-trifluoromethoxyphenyl)-5-methoxycarbonylamino-pyrazole of the formula

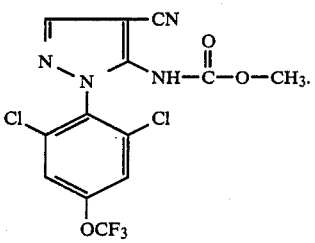

7. A herbicidal composition comprising a herbicidally effective amount of a compound according to claim 1 in admixture with a diluent.

8. A method of combating unwanted vegetation which comprises applying to such vegetation or to a locus from which it is desired to exclude such vegetation a herbicidally effective amount of a compound according to claim 1.

9. The method according to claim 8, wherein such compound is
4-cyano-1-(2,6-dichloro-4-trifluoromethylthiophenyl)-5-methoxycarbonylamino-pyrazole,
1-(2-chloro-4-trifluoromethoxy-phenyl)-4-cyano-5-methoxycarbonylamino-pyrazole,
1-(2-chloro-4-trifluoromethoxy-phenyl)-4-cyano-5-ethoxycarbonylamino-pyrazole, or
4-cyano-1-(2,6-dichloro-4-trifluoromethoxyphenyl)-5-methoxycarbonylamino-pyrazole.

* * * * *

UNITED STATES PATENT AND TRADEMARK OFFICE
CERTIFICATE OF CORRECTION

PATENT NO. : 4,734,122

DATED : March 29, 1988

INVENTOR(S) : Reinhold Gehring, et al.

It is certified that error appears in the above-identified patent and that said Letters Patent is hereby corrected as shown below:

| | |
|---|---|
| Title Page, Abstract, line 1 | Before "5-" insert --Novel substituted-- |
| Col. 1, line 40 | Correct spelling of --halogenoalkyl-- |
| Col. 11, line 36, under "$R^1$" | Delete "$ClCH_3$" and substitute --$ClCH_2$-- |
| Col. 14, line 35 under "$R^7$" | Delete " H O" and substitute --H-- |
| Col. 14, line 35 under "Y" | Insert --O-- |
| Col. 27, line 61 | Correct spelling of --afforestations-- |
| Col. 29, line 22 | After "dichlorophenoxy)" insert -- - -- |
| Col. 31, Table 2, Examples 5, 7 and 9, under "$R^2$" | Delete formula and substitute $$--C_6H_5 - O - \overset{O}{\underset{\|}{C}} --$$ |
| Col. 33, line 40 | Delete "tri-" and substitute --di- -- |

Signed and Sealed this

Thirteenth Day of December, 1988

Attest:

DONALD J. QUIGG

Attesting Officer          Commissioner of Patents and Trademarks

UNITED STATES PATENT AND TRADEMARK OFFICE
CERTIFICATE OF CORRECTION

PATENT NO. : 4,734,122

DATED : March 29, 1988

INVENTOR(S) : Reinhold Gehring, et al

It is certified that error appears in the above-identified patent and that said Letters Patent is hereby corrected as shown below:

Title Page, "Abstract", line 1        Before "5-" insert --Substituted--

Signed and Sealed this

Twenty-eighth Day of March, 1989

Attest:

DONALD J. QUIGG

*Attesting Officer*        *Commissioner of Patents and Trademarks*